US005084042A

United States Patent [19]

McPhee

[11] Patent Number: 5,084,042

[45] Date of Patent: Jan. 28, 1992

[54] MEDICAL SOLUTION CONTAINER OUTLET PORT WITH IMPROVED PIERCEABLE DIAPHRAGM

[75] Inventor: Charles J. McPhee, Huntington Beach, Calif.

[73] Assignee: McGaw, Inc., Irvine, Calif.

[21] Appl. No.: 546,541

[22] Filed: Jun. 29, 1990

[51] Int. Cl.[5] ..................... A61B 19/00

[52] U.S. Cl. ..................... 604/415; 604/403

[58] Field of Search ............... 604/415, 905, 403, 408, 604/411; 215/247

[56] References Cited

U.S. PATENT DOCUMENTS

| | | | |
|---|---|---|---|
| Re. 31,082 | 11/1982 | Winchell . | |
| 2,231,418 | 2/1941 | Trotter . | |
| 2,414,240 | 1/1947 | Page . | |
| 2,777,443 | 1/1957 | Thomas et al. | 215/247 X |
| 2,851,201 | 9/1958 | Poitras et al. . | |
| 2,923,427 | 2/1960 | Klopfenstein . | |
| 3,005,455 | 10/1961 | Poitras et al. . | |
| 3,474,789 | 10/1969 | Soto | 604/415 X |
| 3,642,047 | 2/1972 | Waage . | |
| 3,720,524 | 3/1973 | Nakagami . | |
| 4,089,432 | 5/1978 | Crankshaw et al. | 604/415 X |
| 4,161,949 | 7/1979 | Thanawalla | 604/905 X |
| 4,207,988 | 6/1980 | Prouty et al. . | |
| 4,478,342 | 10/1984 | Slater et al. . | |
| 4,484,916 | 11/1984 | McPhee . | |
| 4,576,602 | 3/1986 | Levin et al. | 604/408 |
| 4,578,074 | 3/1986 | van Leerdam . | |
| 4,591,049 | 5/1986 | Walter et al. . | |
| 4,741,446 | 5/1988 | Miller . | |
| 4,944,736 | 7/1990 | Holtz | 604/403 |

FOREIGN PATENT DOCUMENTS

| | | | |
|---|---|---|---|
| 154846 | 9/1985 | European Pat. Off. | 604/408 |

*Primary Examiner*—Robert A. Hafer
*Assistant Examiner*—Sam Rimell
*Attorney, Agent, or Firm*—Christie, Parker & Hale

[57] ABSTRACT

A medical solution container includes a bag portion for storing solution and a header portion which incorporates an improved outlet port in communication with the bag portion for receiving and holding a spike from an administration set. The outlet port has, at a distal end from the bag portion, a generally inwardly inclined tapered annular collar which, at its widest diameter portion, joins a substantially cylindrical coaxial bore section. The cylindrical bore section has a first section with a reduced diameter which adjoins a second section having an enlarged diameter. The second section is located at an end of the outlet port proximate the bag. A pierceable diaphragm for sealing the outlet port is supported at the junction of the reduced and enlarged diameter bore sections and lies substantially in a plane which is at an angle to a normal to the insertion direction of the spike or the axial direction of the cylindrical bore. By providing the diaphragm at an angle, which is preferably between about 5° and about 20°, the force required to pierce the diaphragm with the spike is reduced while a reliable holding force is maintained after the spike has been inserted, to frictionally hold the spike in the outlet port.

18 Claims, 5 Drawing Sheets

MEDICAL SOLUTION CONTAINER OUTLET PORT WITH IMPROVED PIERCEABLE DIAPHRAGM

FIELD OF THE INVENTION

This invention relates to fluid outlet ports for medical solution containers, such as containers for intravenous (IV) fluids to be administered to a patient, and particularly to fluid outlet ports having a pierceable diaphragm.

BACKGROUND OF THE INVENTION

Containers for storage and administration of medical solutions are well known. Such containers are commonly referred to as partial additive bags or PABs. One such container is disclosed in U.S. Pat. No. 4,484,916 to McPhee, assigned to the present assignee. The container disclosed in the above-mentioned patent is formed of a plastic bag and a molded plastic header section. In the header section, there is an inlet port for admitting medication, nutrients, etc., into the bag, and an outlet port through which the bag's contents may be drawn for ultimate delivery to a patient.

The outlet port is a hollow, substantially cylindrical structure sealed by an internal, pierceable diaphragm. Medication, typically in liquid form, is administered from the container to a patient through IV tubing coupled to the container by means of a filter spike. The combination of IV tubing and spike are usually referred to as "an administration set." The spike, usually formed of a hollow, cylindrical shaft terminated by a tapered tip, is pushed into the outlet port so that the tip pierces the diaphragm. As insertion continues, the spike's cylindrical shaft spreads the diaphragm open as it passes through. During insertion and thereafter, the diaphragm frictionally engages the spike, forming a seal between the diaphragm and the spike to prevent the loss of liquids or air from the bag around the spike's exterior. After the spike is fully inserted, the bag can be turned upside down with the outlet port on the bottom, so that the medical solution can pass through the hollow spike to the IV tubing and, ultimately, to the patient. Frictional engagement between the spike and diaphragm helps to secure the spike in the outlet port.

It is conventional to form the pierceable diaphragm of the above-described outlet port in a plane normal to the axis of the port and, hence, normal to the insertion direction of the spike. However, it has been discovered that the force required to fully insert the spike increases sharply to an undesirably high level at the point where the cylindrical shaft of the spike engages the diaphragm. This sharp increase in resistance to pushing the spike through the diaphragm can be mistaken for the point of full insertion, so that the person discontinues the insertion process. When such a spike is not fully inserted, leakage can occur. Moreover, if insertion falls short of where the cylindrical portion of the spike's shaft fully engages and bears against the ruptured diaphragm, there is a danger that, when the container is suspended upside-down, the spike will slip out of the port, since a substantial part of the force retaining the spike in the port is due to the frictional engagement between spike and diaphragm. Incomplete spike penetration will thus result in waste of fluid, or even waste of the container, and possible contamination of the spike.

These problems are exacerbated by the use of different-diameter spikes. Generally, the greater the diameter of the spike, the greater the penetration force required. Spikes normally range from 3/16-inch to ¼-inch in diameter at the cylindrical portion, with the penetration force needed for the ¼-inch spike being significantly greater than that for the 3/16-inch spike.

One way to reduce the required penetration force is to decrease the thickness of the diaphragm or to weaken the material of the diaphragm, or both. However, this reduces the reliability of the seal created by the diaphragm and can reduce the retention force on a spike which has been inserted. Another way to reduce the insertion force is to increase the diameter of the outlet port with respect to the spike, but this also reduces the retention force. Accordingly, it is difficult to design a port whose diaphragm is more easily penetrable by a spike without also unacceptably reducing the force required to withdraw the spike from the port.

SUMMARY OF THE INVENTION

There is, therefore, provided in accordance with practice of the present invention an outlet port for a medical liquid container which incorporates a pierceable diaphragm that is slanted at an angle to a normal to the insertion direction of a filter spike of an administration set, i.e., the diaphragm is slanted at an angle to a normal to the axial direction of the port. The force required to be exerted on the filter spike to penetrate such a slanted diaphragm is less than the force required to penetrate a diaphragm that is not slanted, while the force retaining the spike within the slanted diaphragm remains acceptably high.

In one embodiment of the invention, the medical solution container is in the form of a collapsible bag incorporating inlet and an outlet ports. The outlet port has a tubular neck, wherein a substantially cylindrically-shaped channel communicates at one end with the inside of the collapsible bag. The other end of the channel is adapted to receive the filter spike. A pierceable diaphragm is disposed in the channel to provide a seal, which is broken as the spike is inserted into the channel and through the diaphragm. The pierceable diaphragm is disposed substantially in a plane at an angle to a normal to the insertion direction of the spike to provide for gradual engagement of the spike's cylindrical shaft with the diaphragm during insertion. Such gradual engagement avoids a sharp increase in the insertion force required to overcome the diaphragm's resistance to spreading. For a presently preferred diaphragm material, the preferred angle is from about 5° to about 20°, and is preferably about 15°.

BRIEF DESCRIPTION OF THE DRAWINGS

These features and advantages of the invention, as well as other features and advantages of the invention, will be more apparent from a reading of the claims and of the detailed description of the invention in conjunction with the drawings described below.

DETAILED DESCRIPTION

Figure 1:
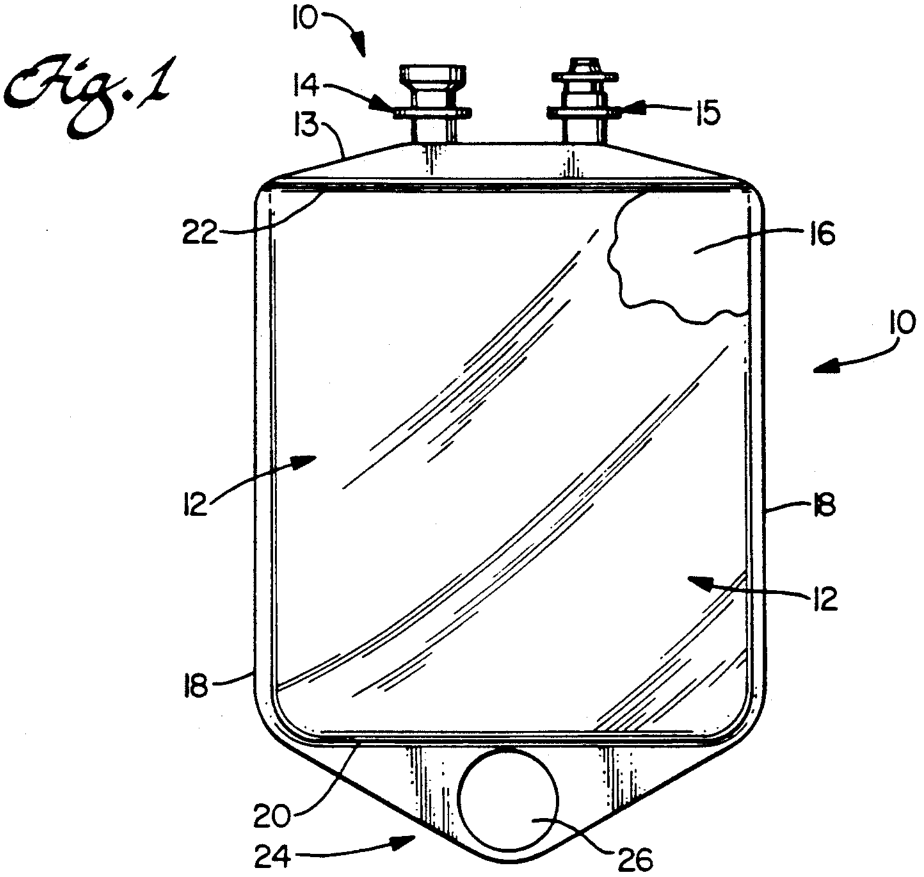
FIG. 1 is a semi-schematic, partially cut-away, side-elevational view of one embodiment of a medical solution container incorporating an outlet port provided in accordance with practice of the present invention.
Figure 2:
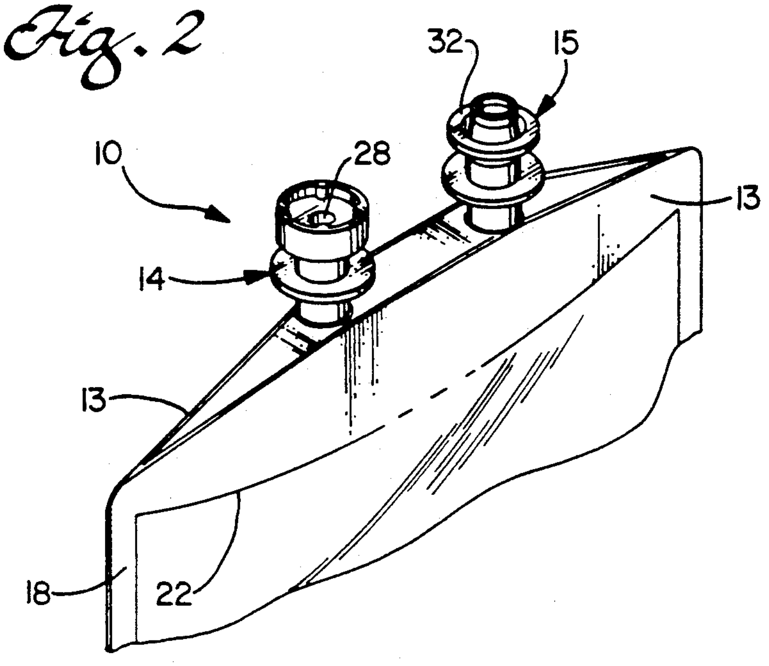
FIG. 2 is a semi-schematic perspective view of the container of FIG. 1, prominently showing the inlet and outlet ports thereof.

Referring to FIG. there is shown a side elevational view of an exemplary embodiment of a medical solution container 10 provided in accordance with practice of principles of the present invention. The container comprises a collapsible bag or pouch portion 12 connected to a header portion 13, from which inlet and outlet ports 14 and 15, respectively, extend. An interior compartment 16, in which a medical solution is stored, is defined within the pouch and header portions of the container.

The container 10 is formed substantially as is described in U.S. Pat. No. 4,484,916, with the outlet port 15 modified in accordance with the invention. U.S. Pat. No. 4,484,916 is incorporated herein by reference.

In an exemplary embodiment, the header 13 is a molded thermoplastic material which has the appropriate properties of flexibility, durability, autoclavability, and inertness. Such materials include polyolefins, particularly propylene-ethylene copolymers such as a polyallomer, provided by Eastman Kodak under the designation "M753-296E," blended with 10% by weight of a styrene butadiene elastomer sold by Shell Chemical Company under the trademark "KRATON." The bag portion 12 comprises two sheets or films of thermoplastic material, heat-sealed to each other along their side and bottom marginal areas or edges 18 and 20, respectively, and heat-sealed to the header 13 along their top marginal areas 22. The end 24 of the container 10 opposite from the header 13 is provided with an opening 26 to facilitate suspension of the container from a hook of a conventional IV stand (not shown).

The inlet port 14 is provided for injecting additives (e.g., medication or nutrients) into the contents (such as a prepackaged dextrose solution) of the container 10. The port 14 has an opening or channel 28 leading to the contents of the container 10, and a resilient self-sealing stopper (not shown) is mounted on the port upstream from the opening 28, through which the additives are injected. Suitable inlet ports are described in U.S. Pat. No. 4,484,916.

The outlet port 15 may be referred to as a set port because it can be used to couple the container 10 to a conventional administration set. As is well known, such an administration set includes a hollow spike (34 in phantom in FIGS. 3 and 4 and in detail in FIG. 5) that is inserted into the set port. Such a spike is frictionally retained by the set port in order that the container 10 may be inverted and suspended, and its fluid contents withdrawn and administered intravenously to a patient. The outlet port 15 can be provided with a sealing disk and a tear-off cap combination (not shown), both of which would be removed prior to insertion of the spike into the port. The sealing disk and cap, which are provided to seal the port 15 to maintain the sterility of the interior of the port prior to use, and which need not be described in any detail to understand the invention, are removed prior to insertion of the spike 34 into the port 15. The port 15 includes a projection 32, which is used in conjunction with the sealing disk and cap arrangement.

Figure 3:
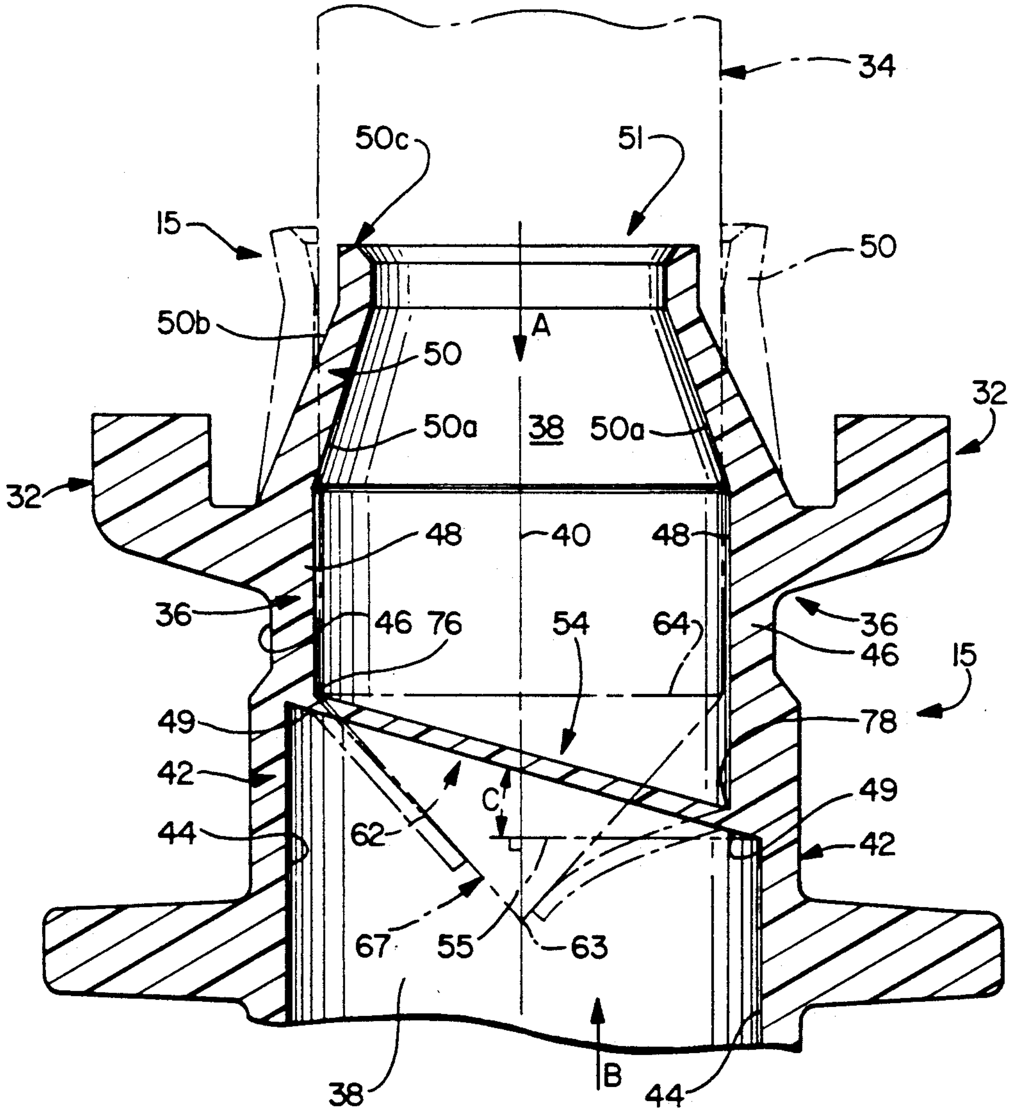
FIG. 3 is a semi-schematic, enlarged, longitudinal sectional view of the outlet port of the container of FIGS. 1 and 2, showing a slanted diaphragm according to one embodiment of the invention and also showing, in phantom, the outlet port as it appears during the spike insertion process shortly after the cylindrical shaft of the spike first meets the diaphragm.
Figure 4:
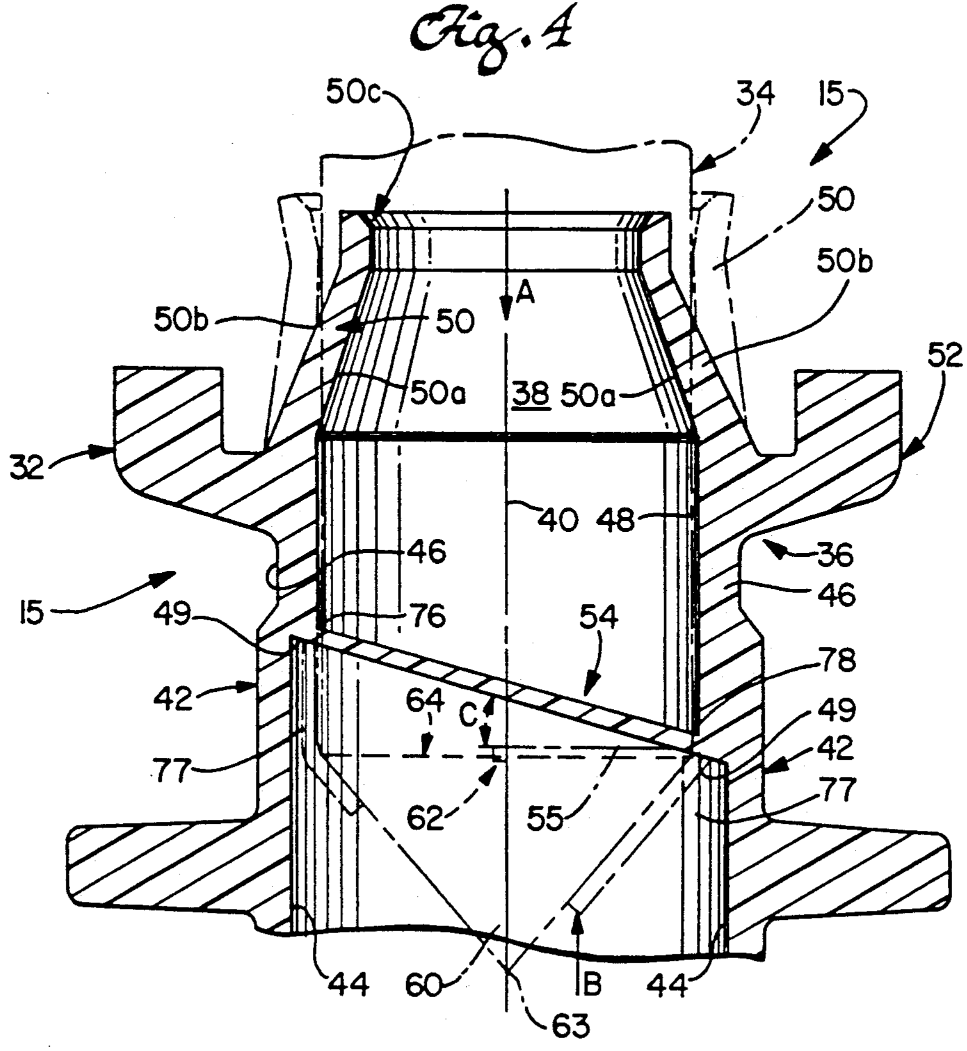
FIG. 4 is a semi-schematic, enlarged, longitudinal sectional view of the outlet port of the container of FIGS. 1 and 2, showing the slanted diaphragm of FIG. 3 and also showing, in phantom, the outlet port assembly as it appears during the spike insertion process shortly after the spike's cylindrical shaft has engaged the entire diaphragm.

With reference to FIGS. 3 and 4, the set port 15 provided in accordance with this invention is shown with the spike 34, located at two different positions during the spike insertion process. The port 15 comprises a hollow tubular neck portion 36 forming an elongated channel 38 with an axis 40 (the longitudinal axis) along its length. The set port 15 and its channel 38 are shaped and dimensioned for receiving and frictionally holding the spike 34.

In one preferred embodiment of a set port 15 provided in accordance with this invention, the neck 36 is formed integrally with the header 16 and includes a lower wall portion 42 with an enlarged cylindrical bore 44 and a central wall portion 46 defining a coaxial cylindrical bore 48, which has a smaller internal diameter than the bore 46. The transition between the bores 44 and 48 forms a downwardly-facing planar ledge 49. A tapered, annular, resilient collar 50 is formed integrally with the neck 36 and extends upwardly from the central wall portion 46. The collar 50 has an inner surface 50*a* that merges with the surface of the bore 48, and an outer surface 50*b*. Both the inner surface 50*a* and outer surface 50*b* slope inwardly (toward the longitudinal axis 40), terminating in a circular lip 50*c*, which defines the opening 51 of the set port. The diameter of the opening 51 is smaller than the internal diameter of the reduced cylindrical bore 48. Consequently, a spike 34, which has an outside diameter that is smaller than the diameter of the bore 48 but larger than the diameter of the opening 51, will engage the collar 50 to cause limited expansion thereof. The spike will be retained, at least in part, by the tensioning of the collar about the spike. This engagement also serves to form a seal.

The set port neck 36 includes a pierceable diaphragm 54, which extends across and seals the channel 38. In an exemplary embodiment, the diaphragm is formed integrally at the junction of the central wall portion 46 and the lower wall portion 42, substantially in the plane of the ledge 49. In accordance with practice of the present invention, the diaphragm 54 is slanted or tilted, i.e., it lies substantially in a plane which is at an angle C to a normal 55 (shown in FIGS. 3 and 4, in phantom) to the insertion direction A. Said another way, the diaphragm 54 lies in a plane which is at an angle C to the normal of the axis 40 or to the insertion direction A of the spike 34. In an exemplary embodiment, where the bore 48 is about ¼ inch in diameter, diaphragms having a thickness in the range of 0.005–0.009 inch are preferred for the material specified herein for the header and associated diaphragm.

The result of having a diaphragm inclined at an angle, such as the angle C, is that the peak or maximum insertion force needed to push a spike through the diaphragm is decreased, compared to the peak force required for insertion of a spike through a comparable diaphragm which is not at an angle, i.e., which is in a plane normal to the axis 40.

Figure 7:
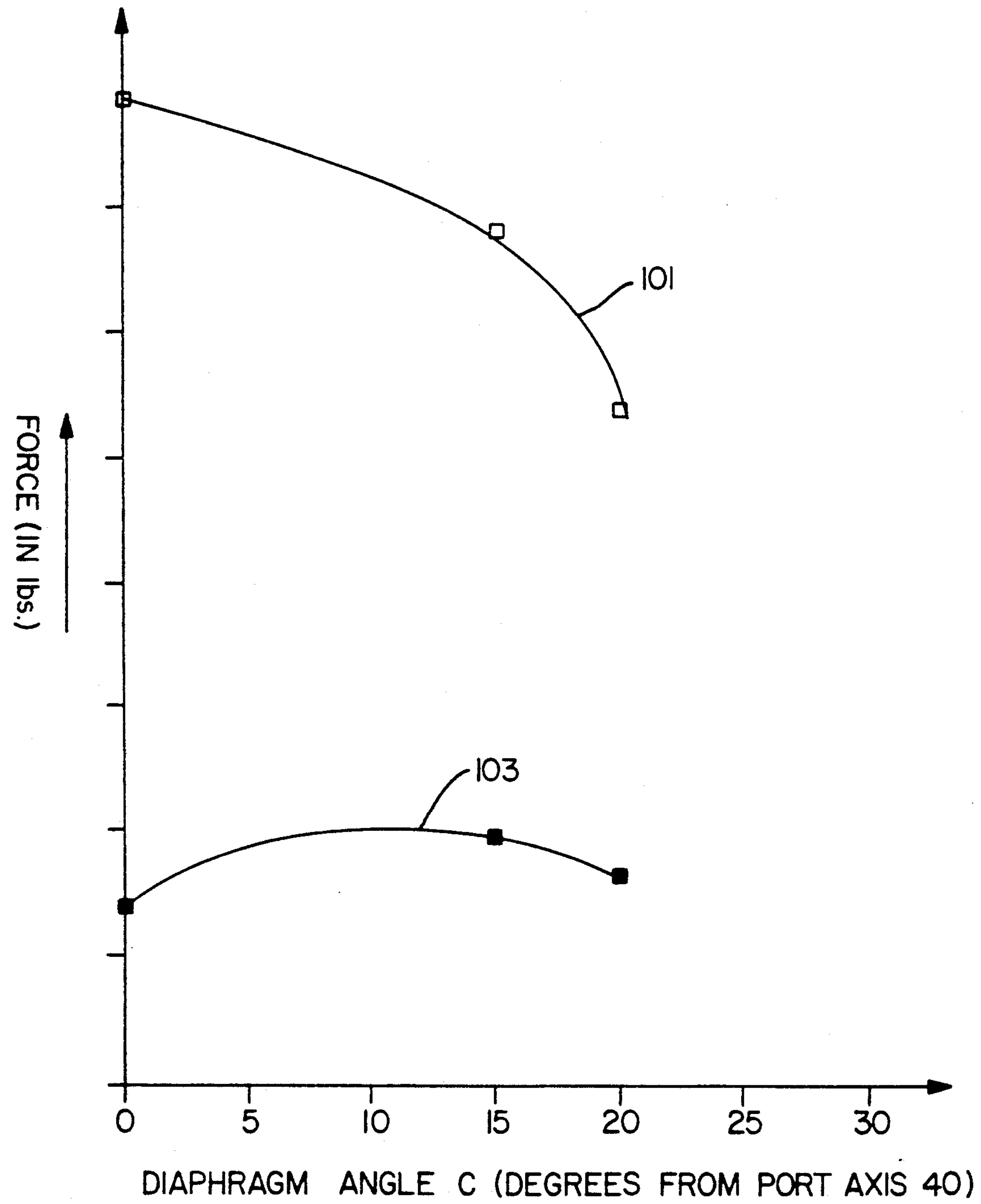
FIG. 7 is a plot of insertion and retention forces against diaphragm angle, as obtained by conducting tests on the outlet port of FIGS. 3 and 4.

FIG. 7 graphically shows the variation in (1) the peak force required to insert a spike (configured like the spike 34) into the outlet port 15 of FIGS. 3 and 4, manufactured from the blend of polyallomer and KRATON described herein, and (2) the force required to retract the spike therefrom, as a function of diaphragm angle. While the plot 101 of insertion force is seen to progressively diminish as the diaphragm inclination angle C is increased, the plot 103 of retraction force peaks at an angle C in the range of between 5° and 15°. When the angle C is less than about 5°, the reduction in insertion force is minimal compared to the reduction at larger angles, and the retraction force is relatively low. The retraction force also falls below its maximum when the angle C exceeds about 15° and falls substantially below its maximum when the angle C reaches 20°. Accordingly, for the outlet port material described herein (the blend of polyallomer with 10% KRATON), the preferred range within which the inclination angle of the diaphragm should be kept, is from about 5° to about 20°, and preferably at about 15°. Of course, with different materials and/or spike dimensions, the optimum range of angles may be wider, narrower, or displaced from that shown.

Figure 5:
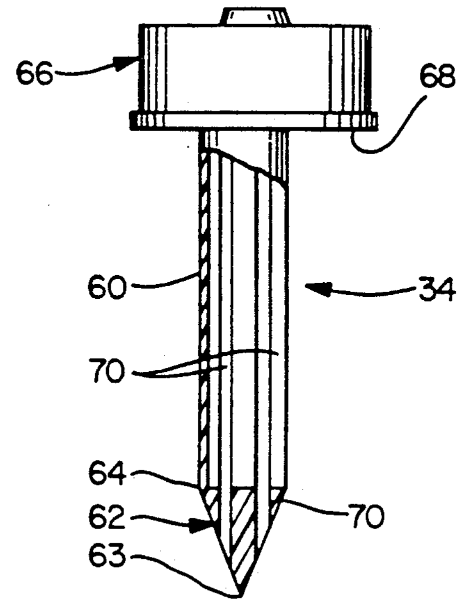
FIG. 5 is a semi-schematic side-elevational, partially cutaway and partially sectional view of a filter spike.

The spike insertion process will be described in more detail following a description of a typical spike 34, shown in a partial cutaway and vertical sectional view in FIG. 5. The spike 34 has a cylindrical shaft 60 terminating in a tapered, and shown here as conical, tip 62, with a point 63 on its end. A circular junction 64 is defined by a line of transition which extends around the spike between its cylindrical shaft and tip portions and which falls in a plane which is normal to the longitudinal axis of the spike. The spike 34 has a top section 66 to which IV tubing (not shown) is connected and which includes a shoulder 68 on its bottom. Two vertical apertures 70 are formed in the spike, extending from the top section 66 for communication with IV tubing, through the conical tip section 62 for communication with the interior compartment 16 of the container 10. (It should be emphasized that the advantages of the invention are not limited to the particular spike described herein.)

With renewed reference to FIGS. 3 and 4, the spike 34 is inserted into the outlet port 15 in the direction A. As the tip 62 enters the channel 38, its conical wall bears against, and spreads open, the annular collar 50. When the spike tip 62 has moved past the lip portion 50c of the collar 50, so that the spike's cylindrical shaft 60 engages and begins passing through the collar lip 50c, the collar 50 is spread to its widest position, as is shown in dashed lines. As insertion continues, the point 63 of the tip 62 meets the slanted diaphragm 54 and pierces and ruptures it. The ruptured diaphragm 54 is folded downward and outward as the tip 62 passes through. FIG. 3 illustrates the instant when the circular junction 64 between the spike's cylindrical shaft 60 and conical tip 62 first engages the ruptured diaphragm 54 and, more particularly, the diaphragm's peripheral junction with the bore 48, which runs along an elliptical path due to the inclination of the diaphragm. The initial engagement between the circular junction 64 of the spike 34 and the diaphragm's periphery occurs at a point 76 on the diaphragm, which is the portion of the diaphragm nearest the opening 51.

The internal diameter of the bore 44 below the diaphragm 54 is larger than the internal diameter of the bore 48 above the diaphragm, so that, as the spike 34 ruptures the diaphragm, the diaphragm material tends to fold or roll downwardly and outwardly, and is accommodated in the space 77 (best seen in FIG. 4) around the inside circumference of the bore 44.

As the insertion of the spike 34 continues, the junction 64 contacts the remaining portion of the diaphragm, with the contact point moving outwardly, in both directions, away from the initial contact point 76, around the circumference of the diaphragm. As the insertion process continues, the junction 64 contacts and pushes through the diaphragm at its lowest point 78, i.e., the point on the diaphragm furthest from the opening 51. The cylindrical shaft 60 pushes the ruptured diaphragm material against the interior surface of the wall 42 in the enlarged bore 44. As can thus readily be appreciated by one of ordinary skill in the art, it is preferred that the enlarged bore have a radius equal to or greater than the radius of the reduced bore 48 by at least the thickness of the diaphragm 54 to provide for accommodation of the diaphragm wall, so that jamming of the spike is inhibited.

The insertion process ends, i.e., the spike is fully inserted, when the shoulder 68 (FIG. 5) of the spike 34 meets lip 50c of collar 50. As is well known in the art, the spike and the set port are dimensioned so that, at this point, the channels 70 are open into the interior compartment 16 of the container 10. In addition, the spike 34 must be retained in the set port so that container 10 can be inverted. In the set port provided in accordance with the present invention, the force retaining the spike 34 in the port 15 results both from frictional engagement of the spike 34 with the ruptured diaphragm 54 and from the frictional engagement between the spike and the collar 50.

From the above description of the insertion process, significant advantages of the invention over conventional set ports are evident. In particular, an important advantage of the invention is that the peak or maximum force required to insert the spike is reduced, as compared to the peak force required with a set port having a conventionally oriented diaphragm. In such a conventional set port, a large increase in insertion force is required (the peak force) when the cylindrical shaft of the spike meets the diaphragm, because the entire circumference of the diaphragm is contacted at the same time by the entire circumference of the junction 64 between the conical point and cylindrical shaft of the spike. This occurs with conventionally-oriented diaphragms because both the junction 64 of the spike and the line along which the diaphragm is attached to the junction of the wall portions of the port lie in planes which are normal to the insertion direction of the spike. As the material at the circumference of the diaphragm is supported by the set port wall, it is difficult to bend downward, particularly when it must bend all at once, as is the case when prior-art diaphragm configurations are used. Requiring the circumferential diaphragm material to be pushed or bent downwardly at the same time causes the sharp rise in the insertion force.

Conversely, the use of a slanted diaphragm in accordance with the invention results in a the required peak insertion force being relatively less. This is due to the progressive engagement of the junction 64 with the diaphragm, so that the circumferential diaphragm material is not contacted and bent downwardly at the same time. The reduced peak insertion force resulting from the arrangement of the present invention promotes complete penetration of the diaphragm by the spike. Such complete penetration is important to ensure that the ruptured diaphragm participates fully in retaining the spike 34 within the outlet port. As noted above, when in use, the IV bag is suspended port end down, so the spike will be pulled downward by gravity and by the downward pressure from the IV liquid flow, as well as by any forces created by jostling of the IV tubing. Without proper frictional retention, fluid may leak or the spike may become disengaged and fall out of the set port. Either of these events can waste the IV bag and its contents and contaminate the spike.

Figure 6:
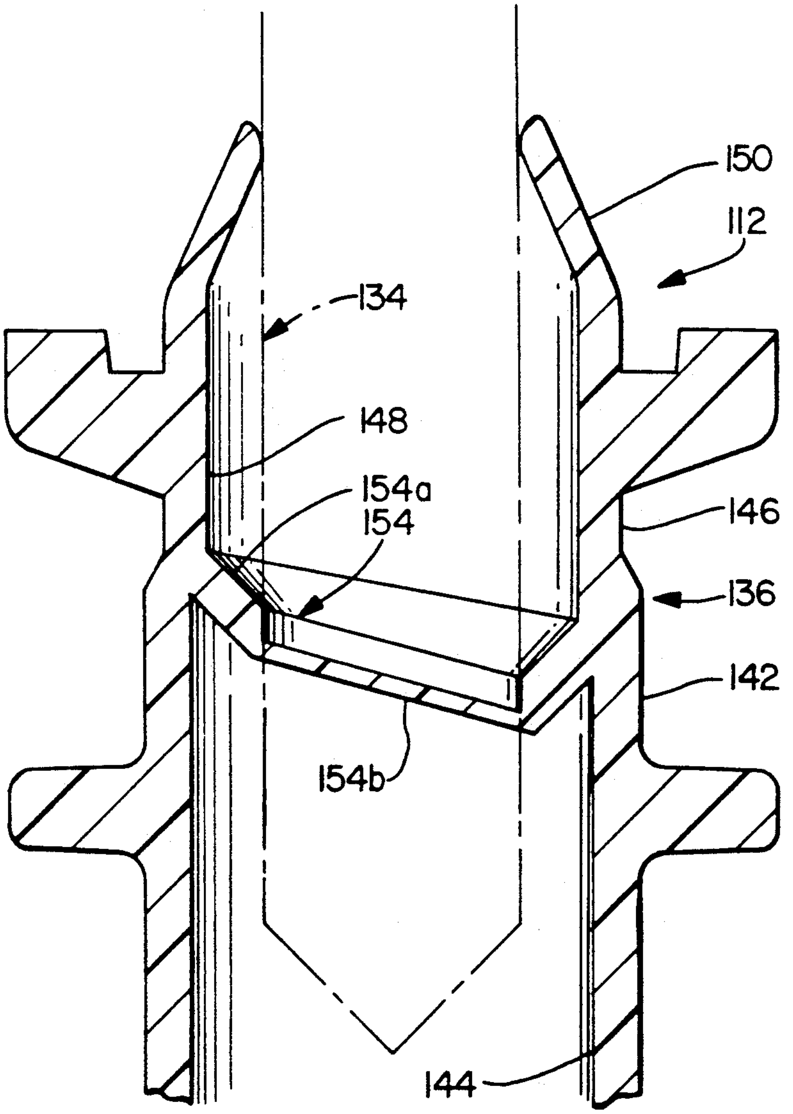
FIG. 6 is a semi-schematic, enlarged, longitudinal sectional view of a second embodiment of an outlet port provided in accordance with practice of the present invention wherein the outlet port diaphragm has a thin central portion and a thicker peripheral portion.

A second embodiment of the invention is shown in FIG. 6. Most of its elements are similar to corresponding elements in the outlet port of FIGS. 3 and 4 and bear the same reference numerals except for being incremented by 100, so that, for example, the neck 36 of FIGS. 3 and 4 appears as the neck 136 in FIG. 6. In accordance with the invention as implemented in the port of FIG. 6, the diaphragm 154 comprises a relatively thick, peripheral, ring portion **154*a* and a relatively thin, central portion 154*b*. For a bore 148 diameter of 0.25 inch, suitable thicknesses for the thin and thick regions 154*b* and 154*a* are in the ranges of about 0005–0.009 inch and 0.020–0.030 inch, respectively. The advantage of this embodiment is that, with the diameter of the thin portion 154*b* just slightly smaller than that of the spike 134 (by from about 0.010 to about 0.020 inch), the retraction force is greater because the thick, peripheral ring portion 154*a* grabs the spike 134** as it is being withdrawn.

While in the foregoing, embodiments of the invention have been disclosed in considerable detail for purposes of illustration, it will be understood by those skilled in the art that many of these details may be varied without departing from the invention as defined by the appended claims.

What is claimed is:

1. A medical solution container comprising a collapsible bag portion and a header portion which define an interior compartment for storing a solution, wherein the header portion incorporates an outlet port which comprises a hollow tubular neck that projects away from the interior compartment and defines a channel extending through the neck to communicate with the interior compartment, the neck being adapted to receive and retain a spike of an administration set inserted in a first direction into the channel, the neck having an inner wall surface for defining the channel and a pierceable diaphragm disposed in the neck for sealing the channel, the diaphragm being oriented substantially in a plane which is at an angle transverse to a normal to the first direction.

2. The container of claim 1, wherein the material comprising the header is a blend comprising about 90% by weight polyallomer and about 10% by weight of a styrene butadiene elastomer, and the angle is within a range of from about 5° to about 20°.

3. The container of claim 1, wherein the material comprising the header is a blend comprising about 90% by weight polyallomer and about 10% by weight of a styrene butadiene elastomer, and the angle is about 15°.

4. The container of claim 1, wherein the inner wall surface of the tubular neck comprises an inwardly tapered annular collar remote from the interior compartment, and wherein the channel comprises an enlarged diameter portion proximate the interior compartment and a reduced diameter portion between the tapered annular collar and the enlarged diameter portion, the pierceable diaphragm being supported at the junction of the reduced and enlarged diameter portions.

5. The container of claim 1, wherein the angle is about 15., and wherein the thickness of the diaphragm is within the range of about 0.005 and 0.009 inch.

6. The container of claim 1, wherein the diaphragm has a uniform thickness.

7. The container of claim 1, wherein the diaphragm has a central portion of a first thickness, and a peripheral portion of a second thickness greater than the first thickness.

8. For use with a medical solution container from which the solution is to be withdrawn through a hollow spike having a cylindrical cross-section, an outlet port comprising a neck member defining a cylindrical channel extending about a longitudinal axis through the neck and a diaphragm sealingly spanning the channel until penetrated by the hollow spike and characterized in that at least a central portion of the diaphragm lies substantially in a plane which is at an angle to a normal to the axis.

9. The outlet port of claim 8, wherein the channel is formed by an inner wall defining a stepped bore having an enlarged bore portion terminating in a reduced bore portion, and wherein the diaphragm is anchored in the inner wall at the junction of the bore portions.

10. The outlet port of claim 9, wherein the inner wall forms a planar ledge where the bore portions meet, and the diaphragm lies substantially in the plane of the ledge.

11. The outlet port of claim 10, wherein the thickness of the diaphragm does not exceed the difference in the radii of the bore portions.

12. The outlet port of claim 9, wherein the diaphragm is anchored in the inner wall along an elliptical path.

13. For use with a medical container, the combination of a spike having a cylindrical shaft terminating in a conical tip at a line of transition which falls in a first plane that is normal to the longitudinal axis of the spike and an outlet port on the container for receiving the spike, the port having a neck member defining a cylindrical channel extending along a longitudinal axis through the neck, and a diaphragm sealingly spanning the channel until penetrated by the spike and characterized in that the diaphragm lies substantially in a second plane which is at an angle to the first plane.

14. The outlet port of claim 13, wherein the channel is defined by a wall having a cylindrical interior surface, and wherein the diaphragm is anchored in the channel wall along an elliptical path defined by the intersection of the second plane with the wall.

15. The outlet port of claim 14, wherein the channel includes a stepped bore comprised of a reduced bore portion opening to an enlarged bore portion along an elliptical ledge, and wherein the elliptical path along which the diaphragm is attached to the wall lies along the elliptical ledge.

16. The outlet port of claim 15, wherein one surface of the diaphragm is coplanar with the ledge.

17. The outlet port of claim 16, wherein the coplanar surface is remote from the side facing the point of entry of the spike into the outlet port.

18. For use with a medical solution container from which the solution is to be withdrawn through a hollow spike having a cylindrical cross-section, an outlet port comprising a neck having a wall defining a cylindrical channel extending about a longitudinal axis through the neck and a diaphragm sealingly spanning the channel until penetrated by the spike and characterized in that the diaphragm lies substantially in a plane and is attached to the wall along a path that lies in a plane which is at an angle to a normal to the longitudinal axis.

* * * * *

UNITED STATES PATENT AND TRADEMARK OFFICE

CERTIFICATE OF CORRECTION

PATENT NO. : 5,084,042

DATED : January 28, 1992

INVENTOR(S) : Charles J. McPhee

It is certified that error appears in the above-identified patent and that said Letters Patent is hereby corrected as shown below:

at column 2, line 34, after "inlet and", delete "an";
at column 3, line 24, after "FIG.", insert -- 1 --;
at column 6, line 64, after "results in", delete "a";
at column 7, line 27, "0005-0.009" should be -- 0.005-0.009 --;
at column 8, line 7, "about 15" should be -- about 15° --;
at column 10, line 2, before "plane", delete "a", and insert -- said --.

Signed and Sealed this

First Day of June, 1993

Attest:

MICHAEL K. KIRK

*Attesting Officer*

*Acting Commissioner of Patents and Trademarks*